(12) United States Patent
Peer et al.

(10) Patent No.: US 6,865,491 B1
(45) Date of Patent: Mar. 8, 2005

(54) METHOD FOR SEQUENCING POLYNUCLEOTIDES

(75) Inventors: Itzhak Peer, Rehovot (IL); Ron Shamir, Rehovot (IL)

(73) Assignee: Ramot at Tel-Aviv University Ltd., Ramot-Aviv (IL)

( * ) Notice: Subject to any disclaimer, the term of this patent is extended or adjusted under 35 U.S.C. 154(b) by 235 days.

(21) Appl. No.: 09/643,407

(22) Filed: Aug. 22, 2000

(51) Int. Cl.[7] .................. G01N 33/48; G06F 19/00; C12Q 1/68
(52) U.S. Cl. .................. 702/19; 702/20; 435/6
(58) Field of Search .................. 702/19, 20; 435/6

(56) References Cited

U.S. PATENT DOCUMENTS

| | | | |
|---|---|---|---|
| 5,492,806 A | 2/1996 | Drmanac | 435/6 |
| 5,525,464 A | 6/1996 | Drmanac | 435/6 |
| 5,667,972 A | 9/1997 | Drmanac | 435/6 |
| 5,695,940 A | 12/1997 | Drmanac | 536/23 |
| 5,873,052 A * | 2/1999 | Sharaf | 702/20 |
| 6,001,562 A | 12/1999 | Milosavljevic | 435/6 |

FOREIGN PATENT DOCUMENTS

| WO | 9004625 | 10/1989 |
|---|---|---|

OTHER PUBLICATIONS

Pe'er,I. et al. "Spectrum Alignment: Efficient Resequencing by Hybridization" Processing of this 8th International Conference on Intelligent Systems for Molecular Biology (ISMB) (2000) PP 1–9.

Bains, W., et al. "A Novel Method for Nucleic Acid Sequence Determination" *J. Theor. Biol.*, vol. 135, p. 303–307, (1988).

Ben–Dor, A., et al. "On the Complexity of Postional Sequencing by Hybridization" *Proc. 10th Int'l. Conf. On Combinatorial Pattern Matching* (CPM '99), p. 88–100, (1999).

Cargill, M., et al. "Characterization of single–nucleotide polymorphisms in coding regions of human genes" *Nature Genetics*, vol. 22, p. 231–238, (1999).

Durbin, R., et al. "Biological Sequence Analysis: Probabilistic models of proteins and nucleic acids" Cambridge University Press, (1998).

Eddy, S.R. "Hidden Markov models" *Current Opinions in Structural Biology*, vol. 6, No. 3, p. 361–365, (1996).

Hirschberg, D.S. "A Linear Space Algorithm for Computing Maximal Common Subsequences" *Communications of the ACM*, vol. 18, No. 6, p. 341–343, (1975).

Jukes, T.H., et al. "Evolutionary Change in Nucleotide Sequences" *Mammalian Protein Metabolism*, New York, Academic Press, p. 21–123, (1969).

Khrapko, K.R., et al. "Oligonucleotide hybridization approach to DNA sequencing" *FEBS Letters*, vol. 256, p. 118–122, (1989).

Kimura, M. "A Simple Method for Estimating Evolutionary Rates of Base ... Nucleotide Sequences", *J. Mol. Evol.*, vol. 16, p. 111–120, (1980).

Krogh, A., et al. "Hidden Markov Models in Computational Biology: Applications to Protein Modeling UCSC–CRL–93–32" Dept. of Computer and Information Sciences, UCSC, (1993).

Krogh, A., et al. "Hidden Markov Models in Computational Biology: Applications to Protein Modeling" *J. Mol. Biol.*, vol. 235, p. 1501–1531, (1994).

Lysov, Y.P., et al. "Determining DNA Nucleotide Sequence by Means of Oligonucleotides Hybridization: A New Method" *Dokl, Acad. Sci.*, USSR, vol. 303, p. 1508–1511, (1988).

Pevzner, P.A., et al. "Towards DNA Sequencing Chips" *Mathematical Foundations of Computer Science, LNCS*, vol. 841, p. 143–158, (1994).

Pevzner, P.A., et al. "Improved Chips for Sequencing by Hybridization" *J. Biomol. Struct. Dyn.*, vol. 9, No. 2, (1991).

Frieze, A.M., et al. "Optimal Reconstruction of a Sequence from its Probes" *Journal of Computational Biology*, vol. 6, No. 3/4, p. 361–368, (1999).

Skiena, S.S., et al. "Reconstructing Strings from Substrings" *Journal of Computational Biology*, vol. 2, No, 2, p. 333–353, (1995).

Smith, T.F., et al. "Identification of Common Molecular Subsequences" *J. Mol. Biol.*, vol. 147, p. 195–197, (1981).

Southern, E.M., et al. "Analyzing and Comparing Nucleic Acid Sequences by Hybridization to Arrays of ... Experimental Models" *Genomics*, vol. 13, p. 1008–1017, (1992).

Southern, E.M. "DNA Chips: Analysing Sequence by Hybridization to Oligonucleotides on a Large Scale" *Trends in Genetics*, vol. 12, p. 110–115, (1996).

Wang, D.G., et al. "Large–Scale Identification, Mapping, and Genotyping of Single–Nucleotide Polymorphisms ... Genome" Science, vol. 280, p. 1077–1082, (1998).

Yang, Z. "Maximum–Likelihood Estimation of Phylogeny from DNA Sequences When Substitution Rates Differ over Sites" Molecular Biology and Evolution, vol. 10, p. 1396–1401, (1993).

(List continued on next page.)

*Primary Examiner*—Marianne P. Allen
*Assistant Examiner*—Channing S. Mahatan
(74) *Attorney, Agent, or Firm*—Ladas & Parry

(57) ABSTRACT

A method for obtaining a nucleotide sequence that is indicative of the sequence of a target polynucleotide molecule T. The method makes use of hybridization data obtained by incubating T with nucleotide probes. A score is assigned to each of a plurality of candidate nucleotide sequences based upon the hybridization data and upon at least one reference nucleotide sequence. A candidate nucleotide sequence in then selected having an essentially maximal score.

32 Claims, No Drawings

OTHER PUBLICATIONS

Milosavljevic, A. "DNA Sequence Recognition by Hybridization to Short Oligomers" J. Computational Biology. vol. 2, No. 2, P 355–370, (1995).

S. Karlin, S.F. Altschul: "Applications and statistics for multiple high–scoring segments in molecular sequences" Proc. Natl. Acad. Sci. USA, vol. 90, pp. 5873–5877, Jun. 1993.

S.F. Altschul, T.L. Madden: "Gapped BLAST and PSI–BLAST: a new generation of protein database search programs" Nucleic Acids Research, 1997, vol. 25, No. 17, pp. 3389–3402.

R.J. Lipshutz: "Likelihood DNA Sequencing by Hybridization" Journal of Biomolecular Structure & Dynamics, ISSN 0739–1102, vol. 11, No. 3(1993).

* cited by examiner

METHOD FOR SEQUENCING POLYNUCLEOTIDES

FIELD OF THE INVENTION

This invention relates to computational methods in molecular biology, and more specifically to methods for determining the sequence of a polynucleotide.

REFERENCES

Baines, W., and Smith, G. C., J Theor. Biology, 135:303–307 (1988).

Ben-Dor, A., Pe'er, I., Shamir, R., and Sharan, R., In Proceedings of the Tenth International Conference on Combinatorial Pattern Matching (CPM '99), 88–100 (1999), New York: ACM Press.

Cargill, M., Altshuler, D., Ireland, J., Sklar, P., Ardlie, K., Patil, N., Lane, C. R., Lim, E. P., Kalyanaraman, N., Nemesh, J., Ziaugra, L, Friedland, L., Rolfe, A., Warrington, J., Lipshutz, R., Daley, G. Q., and Lander, E. S., Nature Genetics, 22:231–238 (1999).

Drmanac, R., and Crkvenjakov, R., Yugoslav Patent Application 570 (1987).

Durbin, R., Eddy, S., Krogh, A., and Mitchison, G., Biological Sequence Analysis: Probabilistic Models of proteins and Nucleic Acids, Cambridge University Press, (1998).

Eddy, S. R., Current Opinions in Structural Biology, 6(3):361–365 (1996).

Hirschberg, D. S., Communications of the ACM, 18,6:341–343 (1975).

Jukes, T. H., and Cantor, C. R., Mammalian Protein Metabolism, New York: Academic Press 21–123 (1969).

Khrapko, K. R., Lysov, Y. P., Khorlyn, A. A., Shick, V. V., Florentiev, V. L., and Mirzabekov, A. D., FEBS Letters, 256:118–122 (1989).

Kimura, M., Journal of Molecular Evolution, 16:111–120 (1980).

Krogh, A., Brown, M. Mian, S., Sjolander, M., and Haussler, D., Applications to protein modeling. Technical Report UCSC-CRL-93-32, Department of Computer and Information Sciences, University of California at Santa Cruz (1993).

Krogh, A., Brown, M., Mian S., Sjolander, M. and Haussler, D., Appliations to protein modeling 235(5):1501-1531 (1994).

Lysov, Y, Floretiev, V., Khorlyn, A., Khrapko, K., Shick, V, and Mirzabekov, A., Dokl, Acad Sci., USSR, 303:1508-1511 (1988).

Macevices, S.C., International Patent Application PS US89 04741 (1989). National Center for Biotechnology Information, 2000, A database of single nucleotide polymorphisms, World Wide Web address: ncbi.nlm.nih.gov/SNP./

Pevzner, P. A., and Lipshutz, R. J., Mathematical Foundations of Computer Science, LNCS 841:143-158 (1994).

Pevzner, P. A., Lysov, Y. P., Khrapko, K. R., Belyavsky, A. V., Florentiev, V. L., and Mirzabekov, A. D., J. Biomol. Struct. Dyn. 7:63–73 (1989).

Preparata, F., Frieze, A., and Upfal, E., Journal of Computational Biology 6(3–4):361–368 (1999).

Skiena, S. S., and Sundaram, G., J. Comput. Biol. 2:333–353 (1995).

Smith, T. F., and Waterman, M. S., Journal of Molecular Biology 147(1):195–197 (1981).

Southern, E. M., Maskos, U., and Elder, J. K., Genomics 13:1008–1017 (1992).

Southern E., UK patent Application GB 8,810,400 (1988).

Southern, E. M., Trends in Genetics 12:110–115 (1996).

Wang, D. G., Fan, J., Siao, C., Berno, A., Young P., Sapolsky, R., Ghandour, G., Perkins, N., Winchester, E., Spencer, J., Kruglyak, L., Stein, L., Hsie, L., Topalogiou, T., Hubbell, E., Robinson, E., Mittrnann, M., Morris, M.S., Shen, N., Kilburn, D., Rioux, J., Nusbaum, C., Lipshutz, R., Chee, M., and Lander, E. S., Science 280:1077–1082.

Yang, Z., Molecular Biology and Evolution 10:1396–1401.

BACKGROUND OF THE INVENTION

Sequencing by hybridization (SBH) is a method for sequencing a polynucleotide such as a DNA molecule (Bains & Smith 1988, Lysov et al. 1988, Southern 1988, Drmanac and Crkvenjakov 1987, Macevics 1989). In this method, a chip, or microarray is used consisting of a surface upon which all possible oligonucleotide probes of a particular length k (referred to herein as "k-mers") are immobilized (Southern 1996). The DNA molecule whose sequence is to be determined, referred to as the "target molecule", is allowed to hybridize to the k-mers on the chip. The target molecule and the k-mers on the chip may all be single stranded molecules. Alternatively, a double stranded target may first be cut into fragments having single stranded "sticky ends", and the k-mers on the chip may be the sticky ends of double stranded molecules. Ideally, a single stranded target or the sticky end of a double stranded target hybridizes to a k-mer on the chip if and only if the sequence complementary to the k-mer occurs somewhere in the target sequence or the sticky end. Thus, in principle, it is possible to experimentally determine the "k-spectrum" of the target (the set of all k-long substrings present in the target). In practice, however, the data are ambiguous due to the ability of the target to bind to k-mers that are only partially complementary to one of its substrings. Thus, any binarization of the hybridization signal will contain errors.

The goal of SBH is to determine the target sequence from the target spectrum. However, even if the target spectrum were error free, the target sequence is not uniquely determined by the spectrum. If the number of sequences consistent with the spectrum is large, there is no satisfactory method to select the true sequence. Theoretical analysis and simulations (Southern et al., 1992, Pevzner and Lipshutz 1994) have shown that even when the spectrum is errorless and the correct multiplicity of each k-mer in the target sequence is known, the average length of a uniquely reconstructible target sequence using a chip of 8-mers is only about two hundred nucleotides, far below the length of a DNA molecule that may be sequenced by electrophoresis.

Let $\Sigma=(A,C,G,T)$ designate the set of nucleotides composing a DNA molecule. M=4 is the "alphabet size". A DNA sequence is a string over $\Sigma$ which is denoted herein between braces (< >). The k-spectrum of a target sequence T of length L, $T=<t_1, t_2, . t_L>$, is the set of all k-long substrings (k-mers) of T. For each k-mer $\bar{x}=<x_1, x_2, . x_k>$ in $\epsilon\Sigma^k$, we define $T(\bar{x})$ to be 1 if $\bar{x}$ is a substring of T, and 0 otherwise. We denote $K=M^k$, the number of k-mers. A hybridization experiment measures, for each k-mer $\bar{x}$ in $\epsilon\Sigma^k$, an intensity of its hybridization with the target.

The result of an SBH experiment may be described by a graph in which each candidate target sequence is represented as a path in a graph (Pevzner et al., 1989). The graph is a directed de-Bruijn graph G(V,E) whose vertices are labeled by all the (k-1)-mers (the set of vertices $V=\Sigma^{k-1}$), and its edges are labeled by k-mers, (the set of edges $E=\Sigma^k$). The edge labeled $<x_1, x_2 \ldots x_k>$ connects the vertex $<x_1, x_2 \ldots x_{k-1}>$ to the vertex $<x_2 \ldots x_k>$. There is a 1—1 correspondence between L-long candidate target sequences and (L−k+1)- long paths in G, whose edge labels comprise the target spectrum. Hereafter, we interchangeably refer to edges and their labels, and also to sequences and their corresponding paths.

Since k-mers may reoccur in the target sequence, the paths do not have to be simple. When the spectrum is perfect and the multiplicities of the k-mers in the spectrum are known, every solution is an Eulerian path (Pevzner et al. 1989). In practice, however, the spectrum is not perfect and the multplicities are not known.

Alternative chip designs (Bains and Smith 1988, Khrapko et al 1989, Pevzner et al 1991, Preparata et al. 1999, Ben-Dor et al. 1999), as well as interactive protocols (Skiena and Sundararn 1995) havebeen suggested, often assuming additional information, in order to reduce the ambiguity of the hybridization-based reconstruction.

Nucleotide sequences from different sources may resemble each other, due to a common ancestral gene. This phenomenon is encountered within a species, between duplicated regions within a genome, and between individuals within a population. Small differences in sequences, referred to as "Single Nucleotide Polymorphisms" or SNPs, efficiently serve as genetic markers that are useful in medicine. Thus the detection and genotyping of SNPs has become an important task of human geneticists. The evolution of homologous sequences from a common ancestral gene is mainly due to nucleotide substitution. Insertions and deletions of nucleotides are also known to have occurred during evolution of homologous sequences, though at lower rates.

A DNA molecule having a known sequence and known to be homologous to a target molecule has not yet been used to reduce the ambiguity of SBH data in order to determine the target sequence.

SUMMARY OF THE INVENTION

In the following description and set of claims, two parameters are considered to be equivalent to each other if they are proportional to each other.

The present invention provides a method for sequencing a target sequence. In accordance with the invention, experimental spectrum data obtained from a DNA chip is combined with sequence information of a reference DNA molecule. The reference molecule is preferably a molecule believed to be homologous with the target. For example, the target sequence may be a mutant gene and the reference sequence the previously sequenced normal gene. As another example, the target sequence may be a human gene and the reference sequence the homologous gene in another organism. A score is defined for each sequence in a set of candidate target sequences based upon a simultaneous comparison of the candidate sequence with the spectrum and with the reference sequence. A candidate target sequence is then selected having a essentially maximal score. Calculating the score does not require knowledge of the multiplicities of the k-mers in the k-spectrum. Moreover, unlike all prior art algorithms, the score does not assume that the spectrum is perfect.

The invention therefore provides a novel probabilistic method that handles imperfect hybridization data with unknown multiplicities. Thus, in accordance with the invention the hybridization of the target T with the k-mer on the DNA chip complementary to $\bar{x}$ is described by probabilities $P_0(\bar{x})$ and $P_1(\bar{x})$ of the observed hybridization signal when T($\bar{x}$)=0, and T($\bar{x}$)=1, respectively The results of a hybridization experiment are described by the "probabilistic spectrum" (PS) defined as the pair $(P_0,P_1)$ of functions $P_i: \Sigma^k \to [0, 1]$. If the experiment were perfect, i.e., if $P_0(\bar{x})$ and $P_1(\bar{x})$ are either 0 or 1 with $P_0(\bar{x})+P_1(\bar{x})$ 1, then the PS would represent the k-spectrum. In practice, however, $P_0(\bar{x})$ and $P_1(\bar{x})$ are both positive There is thus a chance $1-P_0(\bar{x})$ for a false positive (a k-mer ($\bar{x}$) not occurring in T, whose complementary sequence produces a hybridization signal indicative of hybridization) and a chance $1-P_1(\bar{x})$ for a false negative (a k-mer ($\bar{x}$) occurring in T, whose complementary sequence produces a signal indicative of no hybridization). (When handling probabilities, some of which are perfect, problems of division by zero might occur. This is avoided by implicitly perturbing probabilities 0 and 1 to $_\epsilon$ and $1-_\epsilon$.)

The probability of obtaining a specific spectrum PS when T is used as the target is referred to as the "experimental likelihood". The experimental likelihood is calculated assuming that the hybridization results of the target to different k-mer probes are mutually independent. In one embodiment of the invention, an experimental likelihood $L^e(\hat{T})$ is used that does not assume knowledge of the multiplicities of each k-mer in the sequence. $L^e(\hat{T})$ is given by:

$$L^e(\hat{T}) = Prob(PS \mid \hat{T}) = \prod_{\vec{x} \in \Sigma^k} P_{\hat{T}(\vec{x})}(\vec{x}) \qquad (1)$$

Taking logarithms and defining $$\omega(\vec{x}) = \log \frac{P_1(\vec{x})}{P_0(\vec{x})}$$

we can write:

$$\log P_{\hat{T}(\vec{x})}(\vec{x}) = \begin{cases} \log P_0(\vec{x}) & \text{if } \hat{T}(\vec{x}) = 0 \\ \log P_0(\vec{x}) + \omega(\vec{x}) & \text{if } \hat{T}(\vec{x}) = 1. \end{cases} \qquad (2a)$$

Hence, $$\log L^e(\hat{T}) = \sum_{\vec{x} \in \Sigma^k} \log P_0(\vec{x}) + \sum_{\hat{T}(\vec{x})=1} \omega(\vec{x}). \qquad (2b)$$

The first term is a constant (independent of TP), and is omitted hereafter.

In another embodiment, an approximate likelihood $\tilde{L}(\hat{T})$ is used, that is defined as follows: Let $p=e_0 \ldots e_{L-k}$ be the path in G corresponding to $\hat{T}$ and define $$\log \tilde{L}^e(\hat{T}) = \sum_{i=0}^{L-k} \omega(e_i). \qquad (3)$$

$\tilde{L}^e = L^e(\hat{T})$ for a path in which all edges have a multiplicity of 1, and is otherwise an approximation to $L^e(\hat{T})$. $\tilde{L}(\hat{T})$ has the advantage of being easily computable in a recursive manner:

$$\log \tilde{L}^e(e_0, \ldots, e_l) = \log \tilde{L}^e(e_0, \ldots, e_{l-1}) + \omega(e_l) \qquad (4)$$

In yet another embodiment, an experimental likelihood $\underline{L}^e(\hat{T})$ is used that takes into account the multiplicities of edges. In this case, the probabilistic spectrum consists of probabilities $P_i(\bar{x})$, denoting the probability of the observed hybridization signal when the multiplicity of x in the target is i. $\underline{L}^e(\hat{T})$ is defined by:

$$\underline{L}^e(\hat{T}) = Prob(PS \mid \hat{T}) = \prod_{\bar{x} \in \Sigma^k} P_{\hat{T}(\bar{x})}(\bar{x}) \tag{4b}$$

where $\hat{T}(\bar{x})$ is the multiplicity of $\bar{x}$ in $\hat{T}$.

Thus in its first aspect, the invention provides a method for obtaining a candidate sequence, the candidate nucleotide sequence being indicative of a sequence of a target polynucleotide molecule T, T producing a hybridization signal $I(\bar{x})$ upon incubating T with a polynucleotide $\bar{x}$ for each polynucleotide $\bar{x}$ in a set E of polynucleotides, the method comprising the steps of:

(a) for each polynucleotide $\bar{x}$ in the set E of polynucleotides, obtaining a probability $P_0(\bar{x})$ of the hybridization signal $I(\bar{x})$ when the sequence $\bar{x}$ is not complementary to a subsequence of T and a probability $P_1(\bar{x})$ of the hybridization signal when the sequence x is complementary to a subsequence of T; so as to obtain a probabilistic spectrum (PS) of T;

(b) assigning a score to each of a plurality of candidate nucleotide sequences, the score being based upon the probabilistic spectrum and upon at least one reference nucleotide sequence H; and (c) selecting one or more candidate nucleotide sequences having an essentially maximal score.

In its second aspect, the invention provides a program storage device readable by machine, tangibly embodying a program of instructions executable by the machine to perform method steps for obtaining a candidate nucleotide sequence, the candidate nucleotide sequence being indicative of a sequence of a target polynucleotide molecule T, T producing a hybridization signal $I(\bar{x})$ upon incubating T with a polynucleotide x for each polynucleotide $\bar{x}$ in a set E of polynucleotides, the method comprising the steps of:

(a) for each polynucleotide x in the set E of polynucleotides, obtaining a probability $P_0(\bar{x})$ of $I(\bar{x})$ when the sequence $\bar{x}$ is not complementary to a subsequence of T and a probability $P_1(\bar{x})$ of $I(\bar{x})$ when the sequence $\bar{x}$ is complementary to a subsequence of T; so as to obtain a probabilistic spectrum (PS) of T;

(b) assigning a score to each of a plurality of candidate nucleotide sequences, the score being based upon the probabilistic spectrum and upon at least one reference nucleotide sequence H; and (c) selecting a candidate nucleotide sequence having an essentially maximal score.

In its third aspect the invention provides a computer program product comprising a computer useable medium having computer readable program code embodied therein for obtaining a candidate nucleotide sequence, the candidate nucleotide sequence being indicative of a sequence of a target polynucleotide molecule T, T producing a hybridization signal $l(\bar{x})$ upon incubating T with a polynucleotide $\bar{x}$ for each polynucleotide $\bar{x}$ in a set E of polynucleotides, the computer program product comprising:

(a) for each polynucleotide $\bar{x}$ in the set E of polynucleotides, computer readable program code for causing the computer to obtain a probability $P_0(\bar{x})$ of I($\bar{x}$) the sequence x is not complementary to a subsequence of T and a probability $P_1(\bar{x})$ of $I(\bar{x})$ when the sequence $\bar{x}$ is complementary to a subsequence of T;

(b) computer readable program code for causing the computer to assign a score to each of a plurality of candidate nucleotide sequences, the score being based upon the probabilistic spectrum and upon at least one reference nucleotide sequence H; and (c) computer readable program code for causing the computer to select a candidate nucleotide sequence having an essentially maximal score.

DETAILED DESCRIPTION OF PREFERRED EMBODIMENTS

First Embodiment

In this embodiment, the unknown target sequence $T = <t_1 \ldots t_1>$ has a known, homologous reference sequence $H = <h_1 \ldots h_1>$. H and T are known to differ from each other by nucleotide substitutions without insertions or deletions (indels). This would be the case, for instance, when the target T is a mutant sequence whose wild type sequence H has already been sequenced, and one expects that nucleotide substitutions are the only cause of variability between H and T (statistically, substitutions are much more prevalent than indels (Wang et al. 1998)). A set of M×M position specific substitution matrices $M^{(1)}, \ldots, M^{(1)}$ are used, where for each position j along the sequence:

$$M^{(j)}[i, i'] = Prob(t_j = i \mid h_j = i') \tag{5}$$ for nucleotides i and i'$\in \Sigma$.

for nucleotides i and i'$\in \Sigma$.

The matrices $M^{(j)}$ may be the same for all j, or may different for different positions j. The matrices $M^{(j)}$ are used to calculate a distribution on the space of possible target sequences. This "prior distribution for ungapped homology", $D^U$, is given, for each candidate target sequence T by:

$$D^u(\hat{T}) = Prob(\hat{T} \mid H) = \prod_{j=1}^{l} M^{(j)}[t_j, h_j] \tag{6}$$

One may recursively compute:

$$D^u(\langle t_1 \ldots t_j\rangle) = (\langle t_1 \ldots t_{j-1}\rangle) \cdot M^{(j)}[t_j, h_j] \tag{7}$$

We denote $L^{(j)}[x,y] \equiv \log M^{(j)}[x,y]$.

The probability of a candidate target sequence $\hat{T}$. given the probability spectrum PS and the reference sequence H is:

$$Prob(\hat{T} \mid H, PS) = \frac{Prob(H) \cdot Prob(\hat{T} \mid H) \cdot Prob(PS \mid H, \hat{T})}{Prob(H, PS)} \tag{8}$$

Given $\hat{T}$, the hybridization signal is independent of H:

$$P\,rob(PS \mid H, \hat{T}) = P\,rob(PS \mid \hat{T})$$

Thus, omitting the constant $$\frac{Prob(H)}{Prob(H, PS)}$$

we can write:

$$P\,rob(\hat{T} \mid H, PS) \cong D^u(\hat{T}) \cdot L^e(\hat{T}) \tag{9a}$$

$$P\,rob(\hat{T} \mid H, PS) \cong D^u(\hat{T}) \cdot \underline{L}^e(\hat{T}) \tag{9b}$$

or $$P\,rob(\hat{T}|H,PS) \cong D^u(\hat{T}) \cdot \underline{L}^e(\hat{T}) \quad (9c)$$

Taking logarithms, the following "ungapped scores" of a candidate target are obtained:

$$Score_1^u(\hat{T}) = \log L^e(\hat{T}) + \log D^u(\hat{T}) \quad (10a)$$

$$Score_2^u(\hat{T}) = \log \tilde{L}^e(\hat{T}) + \log D^u(\hat{T}) \quad (10b)$$

$$Score_3^u(\hat{T}) = \log \underline{L}^e(\hat{T}) + \log D^u(\hat{T}) \quad (10c)$$

With $Score^u{}_1$, $Score^u{}_2$ or $Score^u{}_3$, the higher the score of a sequence $\hat{T}$, the more likely it is to be the target sequence. The highest scoring candidate sequence may be determined by any method known in the art. In the search for the highest scoring candidate sequence, complexity is preferably reduced by deleting from the graph edges for which $\tilde{L}^e(\hat{T})$ $L^e(\hat{T})$ or $\underline{L}^e(\hat{T})$ is less than a predetermined constant. Isolated vertices corresponding to highly improbable (k−1)-mers, are also preferably deleted from the graph.

For example, using $\tilde{L}^e(\hat{T})$, the search for a high scoring candidate sequence may be performed by the following algorithm referred to herein as "Algorithm A". In accordance with Algorithm A, for each vertec $\vec{y} = \langle y_1 \ldots y_{k-1} \rangle \in \Sigma^{k-1}$, and integer j=k−1, k, k+1, ..., l, let $S^u[\vec{y},j]$ be the maximum score of a j-long sequence ending with $\vec{y}$ aligned to $\langle h_1 \ldots h_j \rangle$.

Initialize, for each $\vec{y}$:

$$S^u[\vec{y}, k-1] = \sum_{j=1}^{k-1} L^{(j)}[y_j, h_j] \quad (11)$$

Loop over j=k, ..., l, and for each vertex $\vec{y} = \langle y_1 \ldots y_{k-1} \rangle$ recursively update:

$$S^u[\vec{y}, j] = L^{(j)}[y_{k-1}, h_j] + \max_{e=(\vec{z},\vec{y}) \in E}\{S^u[\vec{z}, j-1] + \omega(e)\} \quad (12a)$$

Finally, return:

$$\text{MAX}Score^u = \max_{\vec{y} \in V} S^u[\vec{y}, l] \quad (12b)$$

A sequence T* attaining the maximal score is found from the matrix $S^u$ as is known in the art, for example, by saving trace-back pointers:

$$P[\vec{y}, j] = \underset{\vec{z}=\langle z_0 z_1 \ldots z_{K-1}\rangle, E=(\vec{z},\vec{y}) \in c}{\operatorname{argmax}} \{S^u[\vec{z}, j-1] + \omega(e)\} \quad (13a)$$

$$\text{MAXPtr} = \underset{\vec{y} \in V}{\operatorname{argmax}} S^u[\vec{y}, l] \quad (13b)$$

The maximum-scoring path in the graph is then followed, by setting:

$Z^l$=MAXPtr, and for all j =k, ...,l: $Z^{j-1}$=P[$Z^j$,j]. Denote $Z^j = \langle Z^j{}_1 Z^j{}_2 \ldots z^j{}_{k-1} \rangle$.

The final result is the sequence of nucleotides $\langle z^{k-1}{}_1, z^{k-1}{}_2, \ldots z^{k-1}{}_{k-1}, z^k{}_{k-1}, z^{k+1}{}_{k-1}, \ldots z^l{}_{k-1} \rangle$ The time complexity is O(lK), since the maximization in (12a),(13a) is a maximum of only a constant number (four) of terms. Although the complexity is exponential in k, it is constant for a given microarray (currently feasible values re k=8 or 9). Moreover, the complexity scales linearly with the size of the hybridization experimental results, which are part of the input.

Space complexity requires a more elaborate analysis. When naively using this algorithm, it requires O(lK) memory space, which is quite high for current technology microarrays. We now detail how we can modify the algorithm to reduce space complexity.

Observe, that this algorithm consists of two computations: Computing the optimal score (equations (11),(12a) and (12b)), and reconstructing the optimal sequence (equations (13a) and (13b)). The first task, of computing the optimal score alone, is space-efficient: it can be accomplished using space which is linear in the (effective) size of the hybridization experimental data, that is, O([K]) space.

By following the paradigm of Hirschberg (Hirschberg 1975), for example, for linear-space pair-wise alignment, a version of the algorithm is obtained which requires only linear space. The reduced space complexity is traded for time complexity, which increases by an O(log 1) factor.

For each position j =l, 1 'l, ... k, k−1, the score of the entire sequence is decomposed. The total score is represented as a sum of two expressions: the contribution of its (j−k+1)-prefix, which equals the score of this prefix computed by $S^u$, plus the contribution of the corresponding suffix. Formally, for each vertex $\vec{y} \langle y_1 \ldots y_{k-1} \rangle \in V$, let $R^u[\vec{y}j]$ be the maximum contribution to the score of a (l−j+k−1)-long sequence beginning with $\vec{y}$ aligned to $\langle h_{j-k+2} \ldots h_j \rangle$.

Initialize, for each $\vec{y}$:

$$R^u[\vec{y},l]=0 \quad (14)$$

Loop over j=l−1, l−2, ... k−1, and for each vertex $\vec{y} = \langle y_1 \ldots y_{k-1} \rangle$ recursively update:

$$R^u[\vec{y}, j] = \max_{e=(\vec{y},\vec{z}) \in E}\{R^u[\vec{z}, j+1] + \omega(e) + L^{(j+1)}[z_{k-1}, h_{j+1}]\} \quad (15)$$

Observe that, for all k−1 ≤j ≤l $$\text{MAX}\,Score^u = \max_{\vec{y} \in V}\{S^u[\vec{y}, j] + R^u[\vec{y}, j]\} \quad (16)$$

Equation (16) can be used to decompose the problem into two similar problems, of half its size. Recursively solving these sub-problems gives a divide-and-conquer approach for finding the optimal sequence. The linear space algorithm is therefore as follows:

1. If the length l of the target is smaller than some constant C, for example, 25 nucleotides:
   Solve the problem directly, according to the dynamic program of Equations (11), (12a), (12b), (13a) and (13b).

Otherwise,

2. Set $$m = \frac{l+k-1}{2}.$$

3. For each j =k−1, ... ,m:
   Compute $S^u[\vec{y},j]$ (following equations (11) and (12a)) for all $\vec{y}$, re-using space.

4. For each j =1, l-1, ..., m:
   Compute $R''[\vec{y},j]$ (following equations (14) and (15)) for all $\vec{y}$, re-using space.
5. Find $$\vec{y}_m = \underset{\vec{y} \in V}{\operatorname{argmax}} \{S''[\vec{y}, m] + R''[\vec{y}, m]\},$$

thereby computing: MAXScore'', by (16).
6. Recursively compute:
   (a) The optimal sequence aligned to $\langle h_l \ldots h_m \rangle$ ending with $\overline{Y}_m$.
   (b) The optimal sequence aligned to $(h_m \ldots h_l)$ beginning with $\overline{Y}_m$.

Observe, that for each $\vec{y}$, j, the values of $S''[\vec{y},j]$ and $R''\vec{y}j$, are computed a total of log l times. Thus the algorithm takes $O([K]l \log 1)$ time and $O([K])$ space,. using the effective spectrum.

Second Embodiment: substitutions and deletions

In this embodiment, the unknown target sequence $T=\langle t_1 \ldots t_1 \rangle$ differs from the reference $H=(h, . h,)$, by substitutions and deletions only, without insertions.

Denote the probability of initiating a gap right before $h_j$ (aligning $h_j$ to space) is $2^{\alpha_j}$. Similarly, $\beta_j$ is the logarithm of the probability for gap extension at $h_j$. Also define $\hat{\beta}_j=\log(1-2^{\beta_j})$ $\hat{\alpha}j=\log(1-2^{\alpha_j})$. To overcome boundary problems at the ends of the sequence, we extend the alphabet by including left and right space characters: $\overline{\Sigma}=\Sigma \cup \triangleright, \triangleleft$. We augment the reference sequence by the string $\triangleright^k$ on its left and $\triangleleft^k$ on the right. We extend the substitution matrix by using probabilities that force alignment of each of $\triangleright$ and $\triangleleft$ to itself. Formally, we define:

$$\overline{\Sigma^{k-1}} = \Sigma^{k-1} \bigcup \{\vec{xz}|\vec{x} = \triangleright^j, \vec{z} \in \Sigma^{k-1-j}\} \bigcup \{\vec{zx}|\vec{z} \in \Sigma^j, \vec{x} = \triangleleft^{k-1-j}\} \quad (17)$$

We arbitrarily set $\omega(\vec{y})$ to 0 for each $\vec{y} \in \overline{\Sigma^{k-1}} \setminus \Sigma^{k-1}$. Thus, the weighted de-Bruijn graph is naturally extended over $\overline{\Sigma^{k-1}}$, and so is $[G]=([V], [E])$, its effective subgraph. Hereafter, we use the notation [G] for the extended graph. As with the previous embodiment, in order to reduce complexity, edges for which $\hat{L}^e(\overline{T})$ or $L^e(\overline{T})$ is less than E are preferably deleted from the graph. Isolated vertices corresponding to highly improbable (k−1)-mers, are also preferably deleted from the graph.

The search for a high scoring candidate sequence may be performed by the following algorithm referred to herein as "Algorithm B". In accordance with Algorithm B, for each $\vec{y}= y_1 \ldots y_{k-1} \in [V]$, j=k=1, k, k+1, ..., $S^d[\vec{y},j]$ is defined as the maximum score of aligning a sequence ending with $\vec{y}$ to $\langle h_l \ldots h_j \rangle$ where $h_j$ is aligned to a gap (and $y_{-1}$ is aligned to some $h_1 \ldots h_j$). Further $T^d[\vec{x},j]$ is defined as the maximum score of aligning a sequence ending with $\langle y_1 \ldots y_{k-1} \rangle$, to $\langle h_l \ldots h_j \rangle$ where he aligned to $y_{k-1}$. Initialize, for each $\vec{y}$:

$$S^d[\vec{y}, k-1]=-\infty; \quad (19)$$

$$T^d[\vec{y}, k-1] = \begin{cases} 0 & \vec{y} = \triangleright^{k-1} \\ -\infty & \text{otherwise} \end{cases} \quad (20)$$

Loop over j =k, ..., 1, and for each $\vec{y} = \langle y_1, \ldots y_{k-l} \rangle \in [V]$, recursively update:

$$S^d[\vec{y}, j] = \max \{T^d[\vec{y}, j-1] + \alpha a_j, S^d[\vec{y}, j-1] + \beta_j\} \quad (21)$$

$$T^d[\vec{y}, j] = \quad (22)$$

$$L^{(j)}[y_{k-1}, h_j] + \max_{e=(\vec{z}, \vec{y}) \in E} \left\{ \omega(e) + \max \begin{pmatrix} T^d[\vec{z}, j-1] + \hat{\alpha}_j \\ S^d[\vec{z}, j-1] + \hat{\beta}_j \end{pmatrix} \right\}$$

Finally, return:

$$\text{MAX } Score^d = T^d[\triangleleft^{k-1}, l] \quad (23)$$

The complexity of this algorithm is still $O(l[K])$ and a linear space variant can be obtained, as described in the previous embodiment. A sequence $T^*$ attaining the maximal score is then formed from the matrix $T^d$ as is known in the art, for example, by saving trace-back pointers to follow the maximally scoring path in analogous manner to that described in the previous embodiment.

Third Embodiment: Substitutions, Deletions and Insertions.

In this embodiment, a target sequence is determined when the target is known to be obtained from the reference by substitutions, insertions and deletions. The algorithm is an extension of the dynamic programs of the previous embodiments.

Denote by $T_j$ the target prefix whose last nucleotide is aligned to $h_j$ in the reference sequence. Further denote by $a_j$ (respectively $b_j$) the log-probability of initiating (extending) an insertion in the target after $T_j$, and define $\hat{a}_j=1-a_j$, $\hat{b}_j=1=b_j$.

Consider the weighted graph $(G,\omega)$. Define the K×K matrix W as follows:

$$W[\vec{x}, \vec{y}] = \begin{cases} 2^{\omega(\vec{y})} & \text{The } (k-1) - \text{suffix of } \vec{x} \\ & \text{is the } (k-1) - \text{prefix of } \vec{y} \\ 0 & \text{Otherwise} \end{cases} \quad (24)$$

$W[\vec{x}, \vec{y}]$ is thus the probability of moving from $\vec{x}$ to $\vec{y}$ along i edges. The probability of an insertion of length i after $T_j$ is $a_j b_j^i \hat{b}_j$. Suppose that the prefix $T_j$ ends with $\vec{x}$. Then $a_j b_1^{i-1} \hat{b}_j W[\vec{x}, \vec{y}]$ is the probability of $T_{j+1}$ ending with $\vec{y}$ and being i nucleotides longer than $T_j$. The matrix W' governing the stochastic progression from $T_j$ to $T_{j+1}$ is calculated as follows:

$$W' = \hat{a}_j b_j W^2 \hat{b}_j + a_j b_j^2 W^3 \hat{b}_j \ldots \quad (25)$$

$$= \hat{a}_j W + a_j b_j \hat{b}_j W^2 \sum_{i \geq 2} b_j^{i-2} W^{i-2} \quad (26)$$

$$= \hat{a}_j W + a_j b_j \hat{b}_j W^2 (I - b_j W)^{-1} \quad (27)$$

A new weighted graph $(G',\omega')$ is now defined as follows. The vertex set of G is also the vertex set of G'. The edge set E' of G' is the set of all pairs $\vec{x}, \vec{y}$ with $W'[\vec{x}, \vec{y}]>0$. Each such edge $e=[\vec{x},\vec{y}]$ is associated with a weight $w'(e)=\log W'[\vec{x}, \vec{y}]$.

The search for a high scoring candidate sequence may be performed by the following algorithm referred to herein as "Algorithm C". In accordance with Algorithm C, Algorithm B of the second embodiment is applied to (G', ω') instead of (G, ω).

In contrast to G, degrees in G' are not bounded by 4. Therefore, computing each dynamic program cell has complexity O(K) in the worst case, with the total complexity of the algorithm being O(l|E'|). Again, considering only the effective size of the graph allows more efficient computation, taking O(l|[E']|).

Fourth Embodiment: Substitutions, Deletions and Insertions.

In this embodiment, homology between nucleotide sequences is described by Hidden Markov Models (HMMs) using a set Q of Markov chain states with a predefined set of allowed transitions between them. For each level (position along the sequence) j=1, ..., $l_Q$, Q includes three states: $M_j$(match), $I_j$ (insert), and $D_j$ (delete). $M_j$ and $D_j$ can be reached from the three (j−1) (th) level states. $I_j$ can be reached from the three (j)-(th) level states (including a self-loop). Transition probabilities are as described in previous sections, e.g., $a_j$=ProbS($M_j \mapsto I_j$). Additionally, each insert or match state, q, induces a vector of emission probabilities $M^q$, where $M^q[i]$ is the probability that the target nucleotide is i. We denote $L^q[i]$=0 for q=$D_j$, $L^q[i]$ =log $M^q[i]$ otherwise. We write lpb(X)=log Prob(X) for short.

The search for a high scoring candidate sequence may be performed by the following algorithm referred to herein as "Algorithm D". In accordance with Algorithm D, a three dimensional array S is defined, where for each q∈Q,y=⟨$y_1$ ... $y_{k-1}$⟩∈[V]=r=k, ..., L, S[q, $\vec{y}$,r] is defined as the maximum score of an r-long sequence ending with ($y_1$ ... $y_{k-1}$>, whose alignment to the profile ends in q. Thus, initialize:

$$S[q_{start}, \triangleright^{k-1}, k-1]=0 \quad (28)$$

$$S[q, \vec{y}, k-1] = -\infty \text{ for other values of } \vec{y}, q \quad (29)$$

Loop over r=k, ... 1, and for each $\vec{y}$=⟨$y_1$ ... $y_{k-1}$⟩∈[V]$_p$ r≤$l_Q$, recursively update:

$$S[q, \vec{y}, r] = L^q[y_{k-1}] + \max_{\substack{e=(E,q)\in E \\ q'|q' \mapsto q}} \{S[q', \vec{z}, r-1] + lpb(q' \mapsto q) + \omega(e)\} \quad (30)$$

Finally, return:

$$\text{MAX Score} = \max_l \{S[q_{end1} \triangleleft^{k-1}, l]\} \quad (31)$$

A sequence T* is maximal score is then found in a manner similar to that described in the previous embodiments.

This algorithm requires O($l_Q$ ·[K]·L) time and space, where L is an upper bound on the size of the target sequence. As with the previous embodiments, the complexity of this algorithm can be reduced to O($l_Q$ ·[K] ·L log L) time and O($l_Q$ ·[K]) memory. Furthermore, one can consider the dynamic program as filling a $l_Q$ ×L matrix, with a [K]-long vector in each matrix cell. Since all values far from the main diagonal of this matrix should be negligible, preferably only values within a distance less than a predetermined constant R to the main diagonal are calculated, reducing the complexity to O(R($l_Q$+L) ·[K] ·log L) time and O(R($l_Q$+L)·[K]) space.

Fifth Embodiment: Summation over all paths

In this embodiment the graph nodes (HMM states and k-mers) that are most likely to be visited at a certain position along the target sequence are obtained. The "Forward-Backward" algorithm is used (see, e.g., Durbin et al., 1998) providing the likelihood summed over all paths entering a node, instead of the likelihood of the maximum path. The only change to the equation presented thus far is that max operators are changed into log-sum-of-exponents. More specifically, equations (12a), (12b), (15), (16), (20), (21), (29), and (30) are re-written, respectively, as follows:

$$S^u[\vec{y}, j] = L^{(j)}[y_{k-1}, h_j] + \log \sum_{e=(\vec{z},\vec{y})\in E} \exp(S^u[\vec{z}, j-1] + \omega(e)) \quad (12a')$$

$$MAXScore^u = \log \sum_{\vec{y}\in V} \exp(S^u[\vec{y}, l]) \quad (12b')$$

$$R^u[\vec{y}, j] = \log \sum_{e=(\vec{y},\vec{z})\in E} \exp(R^u[\vec{z}, j+1] + \omega(e) + L^{(j+1)}[z_{k-1}, h_{j+1}]) \quad (15')$$

$$MAXScore^u = \log \sum_{\vec{y}\in V} \exp(S^u[\vec{y}, j] + R^u[\vec{y}, j]) \quad (16')$$

$$S^d[\vec{y}, j] = \log(\exp(T^d[\vec{y}, j-1] + \alpha_j) + \exp(S^d[\vec{y}, j-1] + \beta_j)) \quad (20')$$

$$T^d[\vec{y}, j] = L^{(j)}[y_{k-1}, h_j] + \log \sum_{e=(\vec{z},\vec{y})\in E} \exp(\omega(e)) + \log(\exp(T^d[\vec{z}, j-1] + \hat{\alpha}_j) + \exp(S^d[\vec{z}, j-1] + \hat{\beta}_j)) \quad (21')$$

$$S[q, \vec{y}, r] = L^q[y_{k-1}] + \sum_{\substack{e=(E,q)\in E \\ q'|q' \mapsto q}} \exp(S[q', \vec{z}, r-1] + lpb(q' \mapsto q) + \omega(e)) \quad (29')$$

$$MAXScore = \log \sum_l \exp(S[q_{end1} \triangleleft^{k-1}, l]) \quad (30')$$

Sixth Embodiment: Enhancements

In this embodiment the exact likelihood calculated according to Equation 10a of several top-scoring candidates found using the approximated likelihood (Equation 10b) is calculated. These sequences are then re-ranked. This 2-phase filtering is more discriminative than approximated scoring, while still tractable using the formulae presented.

If the score of a dynamic programming cell is very low, that cell probably does not participate in the maximum solution. This allows discarding such cells, without risking loss of the true optimum. Computing time and space may thus be saved.

The invention may be used for simultaneously re-sequencing several short targets, instead of a single long sequence. This scenario arises when considering many exons of a single gene. The invention may also be generalized to deal with DNA chips that do not contain the set of all k-mers.

When the set of oligonucleotides on the microarray is not the set of all k-mers, a graph is constructed consisting, as vertices, instead of all the (k−1)-mers, all the prefixes and suffixes of oligonucleotides on the microarray. Edges in this graph connect two vertices if there is one base pair suffix (suffix) addition to one of them, that makes the other its proper suffix (prefix). The scoring mechanism remains the same. This also applies for oligonucleotides containing "gaps" or "universal bases" (Preparata et al., 1999).

The invention may be used also for sequencing polypeptides. Given a polypeptide chain homologous to a target, and given a collection of probabilities of occurrence of sub-chains along the target, our algorithms will find the optimal candidate target sequence.

EXAMPLE

The invention was implemented and tested on simulated data. Nucleotide substitutions were equiprobable and insertions and deletions were not allowed. As a reference sequence, prefixes of the gene-rich human mitochondrial sequence, (Accession Number J01415) were used. For each reference sequence, the following were generated:

1. A target sequence generated according to a prescribed probability q of substitution, defining the matrix M as 1-q on the diagonal and q/3 elsewhere.
2. An 8-spectrum for the target was generated using the probabilistic spectrum defined by $P_i(\vec{x})=1-p$ if $T(\vec{x})=i$, where p is a fixed probability.

All probabilistic parameters were constant, i.e., position/k-mer independent. For each 8-spectrum and target sequence, candidate sequences were scored using Eq. (10), and a candidate sequence of maximal score was found.

The algorithm was implemented in C++ and executed on Linux and SGI machines. Running times, on a Pentium 3, 600 MHz machine, were roughly 0.121 log l seconds for an l-long reference sequence (ranging from roughly 7 minutes for a 500 bp-long sequence to 2.5 hours for 6 Kb). Only the main memory was used, with the application consuming at most 40 Mb. The graph was not reduced to its effective size. This would have reduced both space and time dramatically, at the expense of possibly missing the truly maximal scoring sequence.

The performance of the algorithm was quantified by the following FIGS. of merit:

1. Full success rate —The fraction of runs for which the target sequence was perfectly reconstructed.
2. $\epsilon$-success rate —The fraction of runs for which the target sequence length 1 was reconstructed with fewer than $\epsilon \cdot 1$ nucleotide errors.
3. Average sequencing error —The fraction of nucleotide errors.

Table 1 presents results for a scenario of distinct, but closely related sequences, e.g., orthologous genes in a pair of primates. We assume perfect hybridization data with 97% sequence similarity (that is q=0.03). The results show that sequences of length up to 2000 can be reconstructed almost perfectly. The non-monotonicity of the figures of merit with respect to the target length is due to sequence contents.

Table 2 presents results for a scenario of SNP-genotyping. The rate of SNPs is assumed to be 1:700 (Wang et al. 1998), and p=2% was used. The results show that a high success rate is achievable even in the presence of spectrum errors.

TABLE 1

| Length | # runs | % full success | % $\epsilon$-success $\epsilon = 10^{-3}$ | % $\epsilon$-success $\epsilon = 2 \cdot 10^{-3}$ | % avg. error |
|---|---|---|---|---|---|
| 500 | 10 | 100 | 100 | 100 | 0.000 |
| 1000 | 10 | 100 | 100 | 100 | 0.000 |
| 1500 | 10 | 100 | 100 | 100 | 0.000 |
| 2000 | 17 | 94 | 94 | 94 | 0.003 |
| 2500 | 13 | 46 | 53 | 69 | 0.295 |
| 3000 | 14 | 71 | 78 | 78 | 0.488 |
| 3500 | 5 | 0 | 20 | 20 | 4.091 |
| 4000 | 13 | 76 | 84 | 84 | 2.173 |
| 4500 | 11 | 9 | 18 | 45 | 0.091 |
| 5000 | 15 | 0 | 13 | 53 | 4.149 |
| 5500 | 7 | 14 | 28 | 71 | 0.119 |

Table 1: Results on simulated date, for different sequence lengths, assuming 97% sequence similarity between the target and the reference, and perfect hybridization data.

TABLE 2

| Length | # runs | % full success | % $\epsilon$-success $\epsilon = 10^{-3}$ | % $\epsilon$-success $\epsilon = 2 \cdot 10^{-3}$ | % avg. error |
|---|---|---|---|---|---|
| 250 | 10 | 100 | 100 | 100 | 0.000 |
| 500 | 10 | 100 | 100 | 100 | 0.000 |
| 750 | 10 | 90 | 90 | 100 | 0.013 |
| 1000 | 10 | 90 | 90 | 90 | 0.010 |
| 1250 | 10 | 90 | 100 | 100 | 0.032 |
| 1500 | 12 | 91 | 100 | 100 | 0.033 |
| 1750 | 10 | 60 | 80 | 80 | 0.109 |
| 2000 | 10 | 60 | 90 | 90 | 4.965 |
| 2500 | 10 | 0 | 80 | 100 | 10.312 |
| 3000 | 10 | 30 | 70 | 90 | 0.230 |

Table 2: Results on simulated data, for different sequence lengths, assuming p = 2% error the hybridization data, with 1:700 sequence difference.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

What is claimed is:

1. A method for obtaining one or more candidate nucleotide sequences, the candidate nucleotide sequences being indicative of a sequence of a target polynucleotide molecule T, T producing a hybridization signal $I(\vec{x})$ upon incubating T with a polynucleotide $\vec{x}$ for each polynucleotide $\vec{x}$ in a set E of polynucleotides, the method comprising the steps of:

(a) for each polynucleotide $\vec{x}$ in the set E of polynucleotides, obtaining a probability $P_o(\vec{x})$ of the hybridization signal $I(\vec{x})$ when the sequence $\vec{x}$ is not complementary to a subsequence of T and a probability $P_1(\vec{x})$ of the hybridization signal when the sequence $\vec{x}$ is complementary to a subsequence of T; so as to obtain a probabilistic spectrum (PS) of T;

(b) assigning a score to each of a plurality of candidate nucleotide sequences, the score being obtained in a calculation using the probablistic spectrum and at least one reference nucleotide sequence H, the score being indicative of the candidate nucleotide sequence being a variant of H and furthermore being indicative of the probability that the candidate would give rise to the hybridization signal $I(\vec{x})$; and (c) selecting one or more candidate nucleotide sequences having a maximal score that is indicative of the sequence of the target polynucleotide molecule T.

2. The method according to claim 1, wherein the polynucleotides $\vec{x}$ in the set E are immobilized on surface.

3. The method according to claim 1, wherein the set E is a set of k-mers.

4. The method according to claim 3 wherein E is the set of all k-mers formed from nucleotides from a predetermined set of nucleotides.

5. The method of claim 4, wherein the predetermined set of nucleotides is selected from the group consisting of (a) adenine, guanine, cytosine, and thymine; and (b) adenine, guanine, cytosine, and uracil.

6. The method according to claim 1, wherein the score of a candidate nucleotide $\hat{T}$ is obtained in a calculation using $L^e(\hat{T})$ where $$L^e(\hat{T}) = \prod_{\vec{x}=E} P_{\hat{T}(\vec{x})}(\vec{x}),$$

wherein $\vec{T}(\vec{x})=0$ if the sequence of $\vec{x}$ is not complementary to a subsequence of $\hat{T}$ and $\hat{T}(x)=1$ if the sequence of $\vec{x}$ is complementary to a subsequence of $\hat{T}$.

7. The method according to claim 1, wherein the score of a candidate sequence $\hat{T}$ is obtained in a calculation using $\tilde{L}^e(\hat{T})$ where log $$\tilde{L}^e(\hat{T}) = \sum_{i=o}^{m} \omega(e_i),$$

wherein $\hat{T}$ contains polynucleotides $e_o, \ldots e_m$ and $$\omega(e_i) = \log \frac{P_1(e_i)}{P_o(e_i)}.$$

8. The method according the claim 1, wherein T and H have a common length.

9. The method according to claim 8, wherein the score of a candidate sequence $\hat{T}$ is obtained in a calculation using $DU(\hat{T})$ where $$D^u(\hat{T}) = \prod_{j=1}^{l} M^{(j)}[t_j, h_j],$$

wherein $M^{(j)}[tj, hj]$, is a probability of a nucleotide $t_j$ in position j of T being replaced with nucleotide $h_j$ in position j of H.

10. The method according to claim 9, wherein the score of a candidate nucleotide sequence $\hat{T}$ is $L^e_{\cdot}(\hat{T})+\log D''(\hat{T})$ and Score''$2(\hat{T})=\log \tilde{L}^e(\hat{T})+\log D''(\hat{T})$.

11. The method according to claim 9, wherein the polynucleotides in the set E are k-mers, and the step of selecting the candidate nucleotide sequence having said maximal score comprises the steps of:

(a) if the length l of the target is greater than a predetermined length, setting $$m = \frac{l+k-1}{2};$$

(b) for each j=k -1, ... m, computing $S''[\vec{y}, j]$ by $$S^u[\vec{y}, j] = L^{(j)}[y_{k-1}, h_j] + \max_{e=(\vec{z},\vec{y})\in E} \{S^u[z, j-1] + \omega(e)\} \text{ for all } \vec{y};$$

(c) for each j=l, l-1, ... m, computing $R''[\vec{y},j]$ by initializing for each y $R^u[\vec{y}, l]=0$ and looping over $$R^u[\vec{y}, j] = \max_{e=(\vec{y},\vec{z})\in E} \{R^u[\vec{z}, j+1] + \omega(e) + L^{(j+1)}[z_{k-1}, h_{j+1}]\}$$

for all $\vec{y}$;

(d) selecting $$\vec{y}_m = \underset{\vec{y}\in V}{\operatorname{argmax}} \{Su[\vec{y}, m] + Ru[\vec{y}, m]\};$$

and (e) computing the optimal sequence aligned to $\langle\langle h_m \ldots h_l\rangle$ ending with $\vec{Y}_m$, and the optimal sequence aligned to $\langle h_m \ldots h_l\rangle$ beginning with $\vec{y}_m$.

12. The method according to claim 10 wherein the polynucleotides in the set E are k-mers and the step of selecting the candidate nucleotide sequence having said maximal score comprises the steps of (a) for each (k–1)-mer $\vec{y}$ calculating $$Su[\vec{y}, k-1] = \sum_{j=1}^{k-1} L(j)[y_j h_j],$$

(b) for each integer j=k, ... l,
(ba) for each polynucleotide sequence ($^y 1, \ldots ^y k-1$),
(baa) calculating $$S^u[y, j] = L^{(j)}[y_{k-1}, h_j] + \max_{e=(\vec{z},\vec{y})\in E} \{S^u[z, j-1] + \omega(e)\}$$

wherein $L^{(j)}[y,h_j]=\log M^{(j)}[y,h_j]$ (bab) selecting a (k–1)-mer $P[\vec{y},h_j]$ satisfying $$P[\vec{y}, j] = \underset{Z=<Z_0 Z_1 \ldots Z_{k-1}>, E=(Z,y)\in e}{\operatorname{argmax}} \{S^u[z, j-1] + \omega(e)\}$$

(c) selecting a (k–1) mer $Z^1$ having a score essentially equal to $$\max_{\vec{y} \in V} Su[\vec{y}, l];$$

(d) for j=k-1, ... 1-1; reclusively calculating (k-1)-mers Zj where $Z_{j-1}=P[Z_j,j]$ and (e) selecting candidate target sequence $<z^{k-1}1, z^{k-1}2, \ldots z^{k-1}k-1, z^k k-1, z^{k+1}k-1, \ldots z^1 k-1>$, where $Z_j = <{}^{zj}1\,{}^{zj}2 \ldots {}^{zj}k-1>$.

13. The method according to claim 12, wherein algebraic equation (12a'), $$S^u[\vec{y}, j] = L^{(j)}[y_{k-1}, h_j] + \log \sum_{e=(\vec{z},\vec{y}) \in E} \exp(S^u[z, j-1] + \omega(e)) \quad (12a')$$

replaces algebraic equation (12a), $$S^u[\vec{y}, j] = L^{(j)}[y_{k-1}, h_j] + \max_{e=(\vec{z},\vec{y}) \in E} \{S^u[z, j-1] + \omega(e)\} \quad (12a)$$

algebraic equation (12b'), $$\text{MAXScore}^u = \log \sum_{\vec{y} \in V} \exp(Su[\vec{y}, l]) \quad (12b')$$

replaces algebraic equation (12b), $$\text{MAXScore}^u = \max_{\vec{y} \in V} S^u[\vec{y}, l] \quad (12b)$$

the algebraic equation (15')

$$R^u[\vec{y}, l] = \log \sum_{e=(\vec{y},\vec{z}) \in E} \exp(R^u[\vec{z}, j+1] + \omega(e) + L^{(j+1)}[z_{k-1}, h_{j+1}]) \quad (15')$$

replaces algebraic equation (15), $$R^u[\vec{y}, j] = \max_{e=(\vec{y},\vec{z}) \in E} \{R^u[\vec{z}, j+1] + \omega(e) + L^{(j+1)}[z_{k-1}, h_{j+1}]\} \quad (15)$$

and algebraic equation (16')

$$\text{MAXScore}^u = \log \sum_{\vec{y} \in V} \exp(S^u[\vec{y}, j] + R^u[\vec{y}, j]) \quad (16')$$

replaces algebraic equation (16)

$$\text{MAXScore}^u = \max_{\vec{y} \in V} \{S^u[\vec{y}, j] + R^u[\vec{y}, j]\}. \quad (16)$$

14. The method according to claim 1, wherein H and T have lengths such that the length of T is less than the length of H.

15. The method according to claim 14, wherein the step of assigning a score to each of a plurality of candidate nucleotide sequences and the step of selecting the candidate target sequence are performed using an algorithm comprising:

(a) setting, for each $\vec{y} = \langle y_1 \ldots y_{k-1} \rangle \in [V], j=k=1, k, k+1, \ldots, 1, S^d[\vec{y}, j]$ as the maximum score of aligning a sequence ending with $\vec{y}$ to $\langle h_1 \ldots h_j \rangle$ where $h_j$ is aligned to a gap (and $y_k\_1$ is aligned to some $h_i \ldots h_j$);

(b) setting $T^d[\vec{x} j]$ as the maximum score of aligning a sequence ending with $\langle y_1 \ldots y_{k-1} \rangle$ where $h_j$ aligned to $y_{k-1}$;

(c) initializing for each $\vec{y}$,:

$$S^d[\vec{y}, k-1] = -\infty; \quad (19)$$

and $$T^d[\vec{y}, k-1] = \begin{cases} 0 & \vec{y} = \triangleright^{k-1} \\ -\infty & \text{otherwise} \end{cases}; \quad (20)$$

(d) looping over j=k, ..., 1, and for each $\vec{y} = \langle (y_1 \ldots y_{k-1}) \rangle \in [V]$, and recursively updating:

$$S^d[\vec{y}, j] = \max\{T^d[\vec{y}, j-1] + \alpha_j, S^d[\vec{y}, j-1] + \beta_j\} \quad (21)$$

$$T^d[\vec{y}, j] = L^{(j)}[y_{k-1}, h_j] + \max_{e=(\vec{z},\vec{y}) \in E} \left\{ \omega(e) + \max \begin{Bmatrix} T^d[\vec{z}, j-1] + \hat{\alpha}_j \\ S^d[\vec{z}, j-1] + \hat{\beta}_j \end{Bmatrix} \right\} \quad (22)$$

and (e) returning:

$$\text{MAXScore}^d = T^d[\triangleleft^{k-1}, 1] \quad (23).$$

16. The method according to claim 15, wherein algebraic equation $$S^d[\vec{y}, j] = \log(\exp(T^d[\vec{y}, j-1] + \hat{\alpha}_j) + \exp(S^d[\vec{y}, j-1] + \hat{\beta}_j)) \quad (20')$$

replaces algebraic equation 20, $$T^d[\vec{y}, k-1] = \begin{cases} 0 & \vec{y} = \triangleright^{k-1} \\ -\infty & \text{otherwise} \end{cases} \quad (20)$$

and algebraic equation (21')

$$T^d[y, j] = L^{(j)}[y_{k-1}, h_j] + \log \sum_{e=(\vec{z},\vec{y}) \in E} \exp(\omega(e)) + \log(\exp(T^d[\vec{z}, j-1] + \hat{\alpha}) + \exp(S^d[z, j-1] + \hat{\beta}_j)) \quad (21')$$

replaces algebraic equation (21)

$$S^d[\vec{y}, j] = \max\{T^d[\vec{y}, j-1] + \alpha_j, S^d[\vec{y} j-1] + \beta_j\} \quad (21).$$

17. The method according to claim 1, wherein H and T have arbitrary lengths.

18. The method according to claim 17, wherein the step of assigning a score to each of a plurality of candidate nucleotide sequences and the step of selecting the candidate target sequence are performed using an algorithm comprising:

(a) defining E' as the set of edges such that $W'[\vec{x},\vec{y}]>0$, wherein $$W' = \hat{a}_j W + a_j b_j \hat{b}_j W^2 (i - b_j W)^{-1} \quad (27)$$

wherein $$W[\vec{x},\vec{y}] = \begin{cases} 2^{w(\vec{y})} & \text{The } (k-1)-\text{suffix of } \vec{x} \\ & \text{is the } (k-1)-\text{prefix of } \vec{y} \\ 0 & \text{Otherwise} \end{cases} \quad (24)$$

and wherein $a_j$ is the log-probability of initiating an insertion in the target after $T_j$, $b_j$ is the log-probability of extending an insertion in the target after $T_j$, where $T_j$ is the target prefix whose last nucleotide is aligned to $h_j$ in the reference sequence, and $$\hat{a}_j = 1 - a_j, \quad \hat{b}_j = 1 - b_j;$$

(b) defining $w'(e) = \log W'[\vec{x},\vec{y}]$;

(c) setting, for each $\vec{y} = \langle y_1 \ldots y_{k-1} \rangle \in [V]$, $j=k-1, k, k+1, \ldots, l$, $S^d[\vec{y} j]$ as the maximum score of aligning a sequence ending with $\vec{y}$ to $\langle h_1 \ldots h_j \rangle$ where $h_j$ is aligned to a gap, and $y_{k-1}$ is aligned to some $h_1 \ldots h_j$;

(d) setting $T^d[\vec{x} j]$ as the maximum score of aligning a sequence ending with $\langle y_1 \ldots h_{k-1} \rangle$ where $h_j$ is aligned to $y_{k-1}$;

(e) initializing, for each $\vec{y}$,:

$$S^d[\vec{y}, k-1] = -\infty; \quad (19)$$

$$T^d[\vec{y}, k-1] = \begin{cases} 0 & \vec{y} = \triangleright^{k-1} \\ -\infty & \text{otherwise} \end{cases}; \quad (20)$$

(f) looping over $j=k, \ldots, l$, and for each $\vec{y} = (y_1 \ldots y_{k-1}) \in [V]$, and recursively updating:

$$S^d[\vec{y}, j] = \max\{T^d[\vec{y}, j-1] + \alpha_j S^d[\vec{y} j-1] + \beta\} \quad (21)$$

$$T^d[\vec{y}, j] = L^{(j)}[y_{k-1}, h_j] + \max_{e=(\vec{z},\vec{y}) \in E}\left\{\omega(e) + \max\left\{\begin{matrix} T^d[\vec{z}, j-1] + \hat{\alpha}_j \\ S^d[\vec{z}, j-1] + \hat{\beta}_j \end{matrix}\right\}\right\} \quad (22)$$

and (g) returning:

$$\text{MAXScore}^d = T^d[\triangleleft^{k-1}, 1] \quad (23) \quad (23).$$

19. The method according to claim 17, wherein the step of assigning a score to each of a plurality of candidate target sequence is performed using an algorithm comprising:

(a) defining S for each $q \in Q$, $\vec{y} = \langle y_1 \ldots y_{k-1} \rangle \in [V]$, $r=k, \ldots$, $S[q,\vec{y},r]$ as the maximum score of an r-long sequence ending with $\langle y_1 \ldots y_{k-1} \rangle$, whose alignment to the profile ends in q;

(b) initializing:

$$D[q_{start} \triangleright^{k-1}] = 0 \quad (28)$$

$$S[q,\vec{y} k-1] = -\infty \text{ for other values of } \vec{y} q; \quad (29)$$

(c) looping over $r=k, \ldots 1$, and for each $\vec{y} = \langle y_1 \ldots y_{k-1} \rangle \in [V]$, $r \leq l_Q$, recursively updating:

$$S[q,\vec{y},r] = L^q[y_{k-1}] + \max_{\substack{e=(E,q) \in E \\ q' | q' \mapsto q}} \{S[q',\vec{z},r-1] + lpb(q' \mapsto q) + \omega(e)\} \quad (30)$$

and (d) returning:

$$\text{MAXScore} = \max_l\{S[q_{end1} \triangleleft^{k-1}, 1]\} \quad (31).$$

20. The method according to claim 19 wherein a Hidden Makov Model of a reference sequence.

21. The method according to claim 19, wherein algebraic equation (29'), $$S[q,\vec{y},r] = \quad (29')$$
$$L^q[y_{k-1}] + \sum_{\substack{e=(E,q) \in E \\ q'|q' \mapsto q}} \exp(S[q',\vec{z},r-1] + lpb(q' \mapsto q) + \omega(e))$$

replaces algebraic equation (29), $$S[q,\vec{y},k-1] = -\infty \text{ for other values of } \vec{y}, q \quad (29),$$

and algebraic equation (30')

$$\text{MAXScore} = \log \sum_l \exp(S[q_{end1} \triangleleft^{k-1}, l]) \quad (30')$$

replaces algebraic equation (30), $$S[q,\vec{y},r] = L^q[y_{k-1}] + \max_{\substack{e=(E,q) \in E \\ q'|q' \mapsto q}} \{S[q',\vec{z},r-1] + lpb(q' \mapsto q) + \omega(e)\}. \quad (30)$$

22. The method according to any one of the previous claims wherein the target comprises two or more polynucleotide molecules.

23. The method according claim 1 comprising computing the exact score $L^e(\hat{T})$ for several candidate sequences chosen according to the value of the approximated score $\tilde{L}^e(\hat{T})$.

24. The method according to claim 1 further comprising a step of deleting candidate sequences having likelihood below a predetermined score.

25. The method according to claim 1, wherein the score of a candidate nucleotide sequence $\hat{T}$ is obtained in a calculation using $L^e(\hat{T})$ where $$L^e(\hat{T}) = \prod_{\vec{x} \in E} P_{\hat{T}(\vec{x})}(\vec{x}),$$

wherein $T(\vec{x}) = r$ if the sequence of $\vec{x}$ is complementary to exactly r subsequences of $\underline{T}$.

26. The method according to claim 1, wherein the set E of polynucleotides does not include all the polynucleotides of a specific length.

27. The method according to claim 1, wherein the set E of polynucleotides includes polynucleotides of different lengths.

28. The method according to claim 1, comprising using the selected one or more candidate nucleotide sequences in a task selected from the group consisting of:
   (a) detecting or genotyping of Single Nucleotide Polymorphisms;
   (b) detecting or genotyping of genetic syndromes or disorders;
   (c) detecting or gentotying somatic mutations; and
   (d) sequencing a polynucleotide whose function is related to the function of the reference polynucleotide.

29. The method according to claim 1, wherein polynucleotides contain gaps, or universal bases.

30. The method according to claim 1, wherein polypeptides are sequenced instead of polynucleotides.

31. A program storage device readable by machine, tangibly embodying a program of instructions executable by the machine to perform method steps for obtaining a candidate nucleotide sequence, the candidate nucleotide sequence being indicative of a sequence of a target polynucleotide molecule T, T producing a hybridization signal $I(\vec{x})$ upon incubating T with a polynucleotide $\vec{x}$ for each polynucleotide $\vec{x}$ in a set E of polynucleotides, the method comprising the steps of:
   (a) for each polynucleotide x in the set E of polynucleotides, obtaining a probability $P_0$ of $I(\vec{x})$ when the sequence $\vec{x}$ is not complementary to a subsequence of T and a probability $P_1(\vec{x})$ of $I(\vec{x})$ when the sequence $\vec{x}$ is complementary to a subsequence of T; so as to obtain a probabilistic spectrum (PS) of T;
   (b) assigning a score to each of a plurality of candidate nucleotide sequences, the score being obtained in a calculation using the probabilistic spectrum and upon at least one reference nucleotide sequence H, the score being indicative of the candidate nucleotide sequence being a variant of H and furthermore being indicative of the probability that the candidate would give rise to the hybridization signal $I(\vec{x})$; and
   (c) selecting one or more candidate nucleotide sequences having a maximal score that is indicative of the sequence of the target polynucleotide molecule T.

32. A computer program product comprising a computer useable medium having computer readable program code embodied therein for obtaining a candidate nucleotide sequence, the candidate nucleotide sequence being indicative of a sequence of a target polynucleotide molecule T, T producing a hybridization signal $I(\vec{x})$ upon incubating T with a polynucleotide $\vec{x}$ for each polynucleotide $\vec{x}$ in a set E of polynucleotides, the computer program product comprising:
   (a) for each polynucleotide $\vec{x}$ in the set E of polynucleotides, computer readable program code for causing the computer to obtain a probability $P_0(\vec{x})$ of $I(\vec{x})$, the sequence $\vec{x}$ is not complementary to a subsequence of T and a probability $P_1(\vec{x})$ of $I(\vec{x})$ when the sequence $\vec{x}$ is complementary to a subsequence of T;
   (b) computer readable program code for causing the computer to assign a score to each of a plurality of candidate nucleotide sequences, the score obtained in a calculation using the probabilistic spectrum and at least one reference nucleotide sequence H, the score being indicative of the candidate nucleotide sequence being a variant of H and furthermore being indicative of the probability that the candidate would give rise to the hybridization signal $I(\vec{x})$; and
   (c) computer readable program code for causing the computer to select a candidate nucleotide sequence having a maximal score that is indicative of the sequence of the target polynucleotide molecule.

* * * * *